United States Patent
Bebiano e Costa et al.

(10) Patent No.: US 11,351,289 B2
(45) Date of Patent: Jun. 7, 2022

(54) INKS FOR 3D PRINTING, METHODS OF PRODUCTION AND USES THEREOF

(71) Applicant: ASSOCIATION FOR THE ADVANCEMENT OF TISSUE ENGINEERING CELL BASED TECHNOLOGIES & THERAPIES (A4TEC) - ASSOCIAÇÃO, Braga (PT)

(72) Inventors: João Pedro Bebiano e Costa, Vila Real (PT); Joana Catarina Da Silva Correia de Oliveira, Braga (PT); Joaquim Miguel Antunes Correia de Oliveira, Braga (PT); Rui Luís Gonçalves Dos Reis, Oporto (PT)

(73) Assignee: ASSOCIATION FOR THE ADVANCEMENT OF TISSUE ENGINEERING CELL BASED TECHNOLOGIES & THERAPIES (A4TEC)—ASSOCIAÇÃO, Braga (PT)

(*) Notice: Subject to any disclaimer, the term of this patent is extended or adjusted under 35 U.S.C. 154(b) by 82 days.

(21) Appl. No.: 16/620,828

(22) PCT Filed: Jun. 11, 2018

(86) PCT No.: PCT/IB2018/054212
§ 371 (c)(1),
(2) Date: Dec. 9, 2019

(87) PCT Pub. No.: WO2018/225049
PCT Pub. Date: Dec. 13, 2018

(65) Prior Publication Data
US 2020/0179561 A1 Jun. 11, 2020

(30) Foreign Application Priority Data
Jun. 9, 2017 (PT) .................................. 110136

(51) Int. Cl.
*A61L 27/22* (2006.01)
*B33Y 70/00* (2020.01)
*B33Y 80/00* (2015.01)

(52) U.S. Cl.
CPC ............. *A61L 27/227* (2013.01); *B33Y 70/00* (2014.12); *A61L 2400/06* (2013.01); *B33Y 80/00* (2014.12)

(58) Field of Classification Search
None
See application file for complete search history.

(56) References Cited

U.S. PATENT DOCUMENTS

| 2015/0307728 A1 | 10/2015 | Omenetto et al. |
| 2020/0188486 A1* | 6/2020 | Da Mota Martins Gon Alves ..... A61K 38/1858 |
| 2020/0262937 A1* | 8/2020 | Lopez Cebral ............ C08J 5/18 |
| 2021/0000982 A1* | 1/2021 | Antunes Correia De Oliveira ..... A61K 9/70 |

FOREIGN PATENT DOCUMENTS

| CN | 106267370 | 1/2017 |
| KR | 101881587 | 7/2018 |
| PT | 107426 | 4/2014 |
| WO | 2014011644 | 1/2014 |
| WO | 2014085725 | 6/2014 |
| WO | 2014144971 | 9/2014 |

OTHER PUBLICATIONS

Agostinacchio et al. (Trends in Biotech., vol. 39, No. 7, pp. 719-730).*
Zheng et al. (J. Mater. Chem., B, 2021, 9, 238-58).*
Derwent World Patents Index, vol. 2014, No. 59, Database accession No. 2014-N97544, XP002784993 & PT107426 A1 (A4 Tec Assoc Advancement Tissue Eng Cell).
Derwent World Patents Index, vol. 2018, No. 53, Database accession No. 2018-58500W, XP002784994 & KR101881587B B1 20180724 (Univ Seoul Nat R & DB Found).
Murphy SV; Atala A, "3D bioprinting of tissues and organs", Nat Biotech., (20140000), vol. 32, No. 8, doi:doi:10.1038/nbt.2958, pp. 773-785.
Kang H-W; Lee SJ; Ko IK; Kengla C; Yoo JJ; Atala A, "A 3D bioprinting system to produce human-scale tissue constructs with structural integrity", Nat Biotech, (20160000), vol. 34, No. 3, doi:doi:10.1038/nbt.3413, pp. 312-319.
Moreira Teixeira LS; Feijen J; Van Blitterswijk CA; Dijkstra PJ; Karperien M, "Enzyme-catalyzed crosslinkable hydrogels: Emerging strategies for tissue engineering", Biomaterials, (20120000), vol. 33, No. 5, doi:doi:10.1016/j.biomaterials.2011.10.067, pp. 1281-1290.
International Search Report and Written Opinion dated Oct. 4, 2018, corresponding to International Patent Application No. PCT/IB2018/054212; 9 pages.

* cited by examiner

*Primary Examiner* — Hope A Robinson
(74) *Attorney, Agent, or Firm* — Leason Ellis LLP

(57) ABSTRACT

The present disclosure relates to a silk-fibroin ink suitable for 3D printing. The ink for 3D printing now disclosed may be used in chemical and pharma industries, medicine, engineering, manufacturing namely for the production of capsules, fibres, membranes, particles, scaffolds, medical devices, microfluidic devices and patient-specific implants.

10 Claims, 7 Drawing Sheets

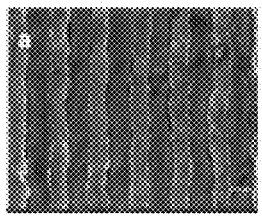
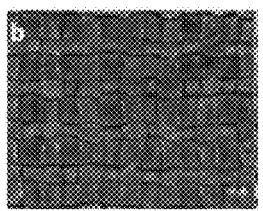
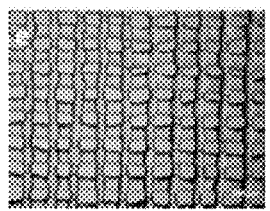
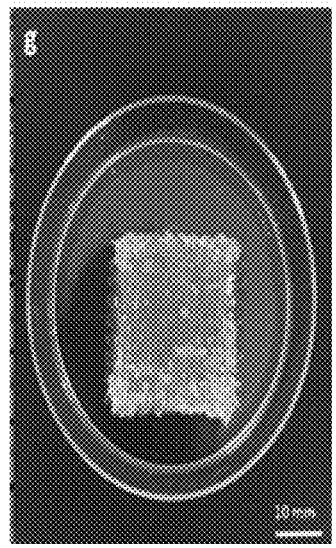
FIG. 5A  FIG. 5B  FIG. 5E
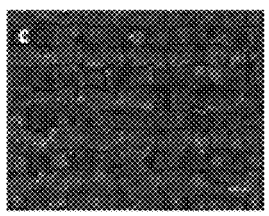
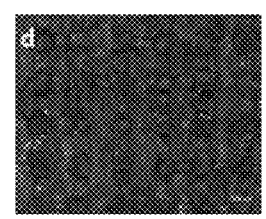
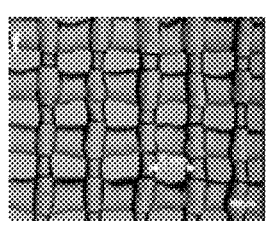
FIG. 5C  FIG. 5D  FIG. 5F  FIG. 5G
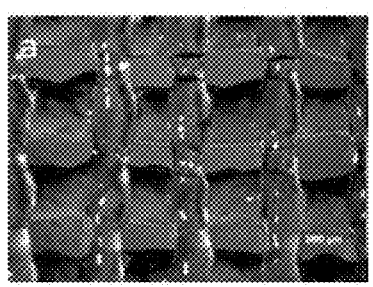
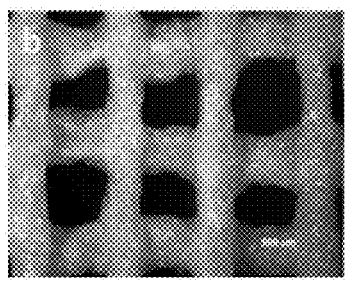
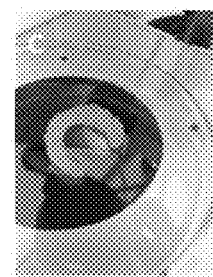
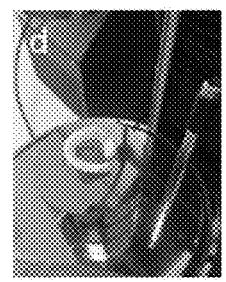
FIG. 6A  FIG. 6B  FIG. 6C  FIG. 6D Micro-CT results of 3D structures after freeze dry. Scale bar: 500 μm

| 3D reconstructions | Mean Porosity (%) | | | Mean pore size (μm) | Mean trabecular thickness (μm) |
|---|---|---|---|---|---|
| | Microporosity | Macroporosity | Total porosity | | |
|  | 26.1 ± 3.2 | 33.1 ± 6.3 | 59.1 ± 3.4 | 224.4 ± 29.2 | 47.8 ± 2.8 |

INKS FOR 3D PRINTING, METHODS OF PRODUCTION AND USES THEREOF

CROSS-REFERENCE TO RELATED PATENT APPLICATIONS

This application is a U.S. National Stage Application under 35 U.S.C. § 371 of International Patent Application No. PCT/IB2018/054212, filed Jun. 11, 2018, which claims the benefit of priority to Portuguese Patent Application No. PT 110136 filed Jun. 9, 2017, both of which are hereby incorporated by reference as if set forth in their respective entireties herein.

TECHNICAL FIELD

The present disclosure relates to a silk-fibroin ink suitable for 3D printing. The ink for 3D printing now disclosed may be used in chemical and pharma industries, medicine, engineering, manufacturing namely for the production of capsules, fibres, membranes, particles, scaffolds, medical devices, microfluidic devices and patient-specific implants.

BACKGROUND 3D printing, an additive manufacturing, is a technology that comprises a computer-assisted approach providing the production of 3D structures. The endless potential of this technology led to its application in many areas, such us, medicine, engineering, manufacturing, etc.

Until now, regarding tissue engineering and medicine regenerative, a large number of materials have been used in 3D Printing (1). Among the natural and biodegradable materials (alginate and gelatin, collagen, chitosan, fibrin and hyaluronic acid, often isolated from animal or human tissues) the alginate, gelatin and hyaluronic acid, due to its properties, are the ones that have been more explored in this field (2). The ideal properties of a bioink comprises several factors, such us, printability, biocompatibility, degradation, mechanical properties and biomimicry (1). Silk fibroin (SF) from the silk worm *Bombyx mori*, has often been used as a textile material, but, in the last few years, this natural biomaterial has gained a lot of attention in the tissue engineering and regenerative medicine area. Its excellent mechanical properties along with its biocompatibility, degradation properties, water-based processing and the presence of easy accessible chemical groups for functional modifications filled almost all the parameters for an ideal material for bioprinting. However, the scientific community still not founded the best processing method in order to print silk fibroin.

These facts are disclosed in order to illustrate the technical problem addressed by the present disclosure.

BRIEF DESCRIPTION 3D printing, an additive manufacturing, is a technology that comprises a computer-assisted approach providing the production of 3D structures. In the field of tissue engineering and regenerative medicine the use of this technique can be a huge advantage even more if it is used a natural material as a bioink. Silk fibroin (SF) has gained a lot of attention in the tissue engineering and regenerative medicine due to its excellent mechanical properties along with its biocompatibility, degradation properties, water-based processing and the presence of easy accessible chemical groups for functional modifications filled almost all the parameters for and ideal material for bioprinting.

The present disclosure relates to the development a methodology that comprises the use of an enzymatically cross-linked approach that provides a silk ink able to be used in 3D printing. This methodology overcomes the facts previously pointed out by referring to the development of an enzymatically cross-linked silk fibroin ink, using horseradish peroxidase and hydrogen peroxide as enzyme and substrate respectively to modify the silk fibroin water solution to be used as a bioink.

This disclosure concerns reliable 3D structures such as scaffolds, patient specific implants, microchips, among others. Besides that, the physicochemical performances of the silk constructs can be tuned for specific uses, by means of using different processing methods after the printing of the 3D constructs as well as the tuned ability provided by the 3D printer itself (Construct Design).

An advantage of using this methodology is the capability to print the silk constructs in an amorphous state giving the opportunity to induce the β-sheet conformation in many different ways.

This is the first time such methodology is used for the production of silk fibroin enzymatically cross-linked inks to be used in 3D printing technology.

The process of production is depicted in FIG. 1 and comprises the following steps:
- preparing 10% to 20% (v/v) of an aqueous silk fibroin (SF) solution concentration to be defined according to final intended features It can be used
- by adding of horseradish peroxidase from 4% to 6% (v/v) (40-60 µL/ml of silk solution) and hydrogen peroxide from 1.5% to 3.5% (v/v) (15-35 µL/ml of silk solution) in 3D Printer cartridge;
- by incubating the whole system at 37° C. for 30-45 minutes for the complete formation of the hydrogel;
- 3D printing of architectures using a silk fibroin enzymatically cross-linked hydrogel (FIGS. 2A-2F).

In an embodiment, 10% (v/v) of an aqueous silk fibroin may be used for soft tissues/cartilage.

In an embodiment, 15% (v/v) of an aqueous silk fibroin may be used for hard cartilage or tissues that will be subjected to high mechanical forces.

In an embodiment, 20% (v/v) of an aqueous silk fibroin may be used for bone repair.

As described before, SF inks is produced using a peroxidase mediated cross-linking method. The horseradish peroxidase (HRP)/hydrogen peroxide ($H_2O_2$) cross-linking approach is used in polymers containing or functionalized with phenol group-containing molecules, including tyrosine, tyramine or aminophenol (3). Considering that SF contains these groups, it was explored this feature in order to develop a bioink. SF ink was combined with horseradish peroxidase solution (HRP type VI, 0.84 mg/mL) and hydrogen peroxide solution ($H_2O_2$, 0.36 wt. %; Panreac, Barcelona, Spain).

In an embodiment, the physicochemical performances of the silk constructs can be tuned for specific uses, by means of using different processing methods after the printing of the 3D constructs as well as the tuned ability provided by the 3D printer itself (Construct Design). One big advantage of using this methodology is the capability to print the silk constructs in an amorphous state giving the opportunity to induce the β-sheet conformation in many different ways.

This is the first time such methodology is used for the production of silk fibroin enzymatically cross-linked inks to be used in 3D printing technology.

The present disclosure relates to an ink comprising a silk fibroin enzymatically cross-linked hydrogel comprising an aqueous solution of silk fibroin.

In an embodiment, the ink may comprise 7-20% (v/v) of the aqueous solution of silk fibroin, preferably 8-18% (v/v), more preferably 11-15% (v/v), in particular wherein the molecular weight of the silk fibroin is 300-350 kDa.

In an embodiment, the ink may also comprise 10-20% (v/v) of the aqueous solution of silk fibroin.

In an embodiment, the ink may comprise a partial β-sheet conformation.

In an embodiment, the ink may comprise 0.1-10% (m/v) of keratin, preferably 0.5-5% (m/v), more preferably 1-3% (m/v), in particular wherein the molecular weight of the keratin is 40-60 kDa.

In an embodiment, the ink may comprise 0.1-10% (m/v) of elastin, preferably 0.5-5% (m/v), more preferably 1-3% (m/v), in particular wherein the molecular weight of the elastin is 40-60 kDa. The advantage of using elastin is that it helps to mimetic, for example, the intervertebral disc.

In an embodiment, the ink now disclosed may have a viscosity of 100 kPa·s$^{-1}$-0.1 Pa·s$^{-1}$ as a function of shear rate at 25° C. The viscosity was measured by a Kinexus pro+ rheometer (Malvern Instruments. UK) and using the acquisition software rSpace (Malvern Instruments, UK) at 25° C.

In an embodiment, the ink may have a loss modulus (G') of 50-1500 Pa at 25° C.

In an embodiment, the ink may have a storage modulus (G") of 10-100 Pa at 25° C. The oscillatory tests was measured by a Kinexus pro+ rheometer (Malvern Instruments, UK) and using the acquisition software rSpace (Malvern Instruments, UK) at 25° C.

In an embodiment, the hydrogel may be a capsule, fibre, coating, membrane, particle, scaffold, medical device, microfluidic device or patient-specific implant.

The present disclosure also relates to a method to prepare the ink comprising a silk fibroin enzymatically cross-linked hydrogel, wherein said method comprises the following steps:
  preparing 7-20% (v/v) of the aqueous solution of silk fibroin, preferably 8-18% (v/v), more preferably 11-15% (v/v) of an aqueous solution of silk fibroin;
  adding 4%-6% (v/v) of horseradish peroxidase and 1.5%-3.5% (v/v) of hydrogen peroxide to the aqueous silk fibroin solution;
  incubating the mixture at 37° C. for 30-45 minutes for the complete formation of the hydrogel;
  freeze-drying at −80° C. for 3 days.

In an embodiment, the horseradish peroxidase is horseradish peroxidase type VI.

In an embodiment, the method now disclosed may further comprise a step of adding 1-3% (m/v) of keratin.

In an embodiment, the method now disclosed may further comprise a step of adding 1-3% (m/v) of elastin.

This disclosure also relates to the use of the ink now disclosed for 3D printing.

BRIEF DESCRIPTION OF THE DRAWINGS

The following figures provide preferred embodiments for illustrating the description and should not be seen as limiting the scope of disclosure.

FIGS. 2A-2F—3D Printing of 3D structures. 2-layer cube shape structure before freeze-drying (FIG. 2A) and after freeze-drying (FIG. 2B). 6 layer cube shape (30×30 mm) 3D structure (FIG. 2C). 6 layer cube shape (5×5 mm) structure after freeze-drying (FIG. 2D). Human meniscus implant before freeze drying (FIG. 2E) and after freeze-drying (FIG. 2F). Scale bars: 500 μm (FIGS. 2A and 2B); 1 mm (FIGS. 2D-2F); 10 mm (FIG. 2C).

FIGS. 5A-5G—Printed structures using S16 ink. 1 layer (FIG. 5A), 2 layers (FIG. 5B), 4 layers (FIG. 5C), and 5 layers cube shape printed structure (FIG. 5D). stereomicroscope images from 2 layers structures (FIGS. 5E-5F). FIG. 5G: 8 layers cube shape structure (30×30×4 mm).

FIGS. 6A-6D—3D printed structures before (FIGS. 6A and 6C) and after freeze-drying (FIGS. 6B and 6D).

DETAILED DESCRIPTION

The present disclosure relates to a silk-fibroin ink suitable for 3D printing. The ink for 3D printing now disclosed may be used in chemical and pharma industries, medicine, engineering, manufacturing namely for the production of capsules, fibres, membranes, particles, scaffolds, medical devices, microfluidic devices and patient-specific implants.

In an embodiment, the rheological properties of silk inks were determined as follows.

In an embodiment, the enzymatically cross-linked silk inks is subjected to high shear forces when used in 3D direct printing. The inks should have a shear-thinning behaviour in order to, not only ensure the filament shape during the printing process but also the correct flow through the nozzle.

In an embodiment, two different concentrations of silk were used for these tests 16% (v/v) and 8% (v/v).

Figure 1:
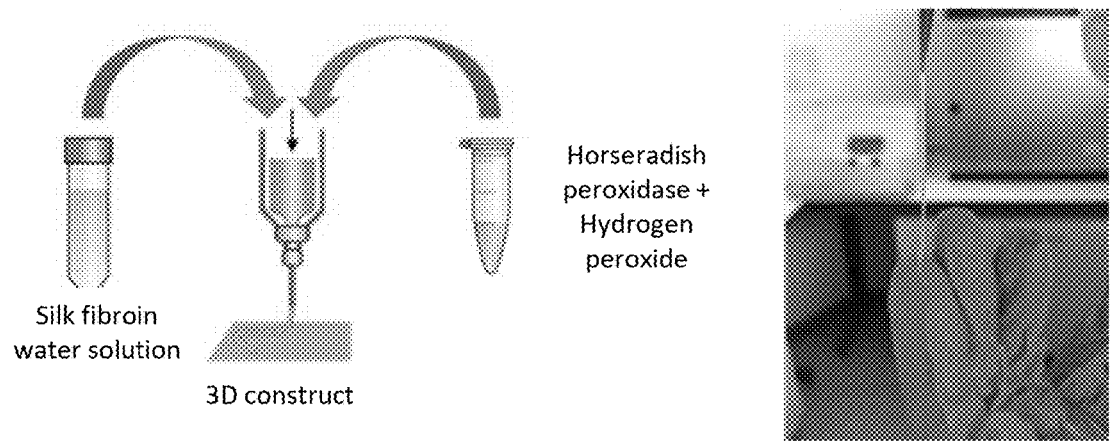
FIG. 1—Schematic representation of the preparation of SF ink for 3D printing.
Figures 2A, 2C, 2E:
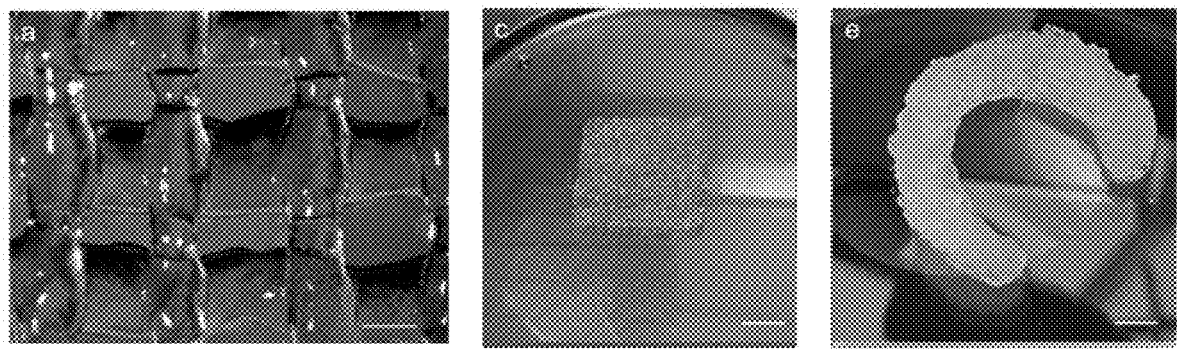
Figures 2B, 2D, 2F:
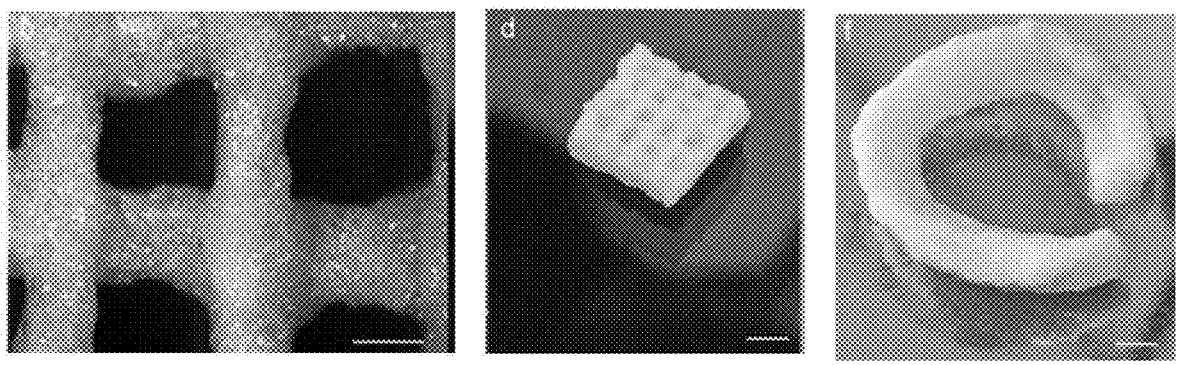
Figure 3:
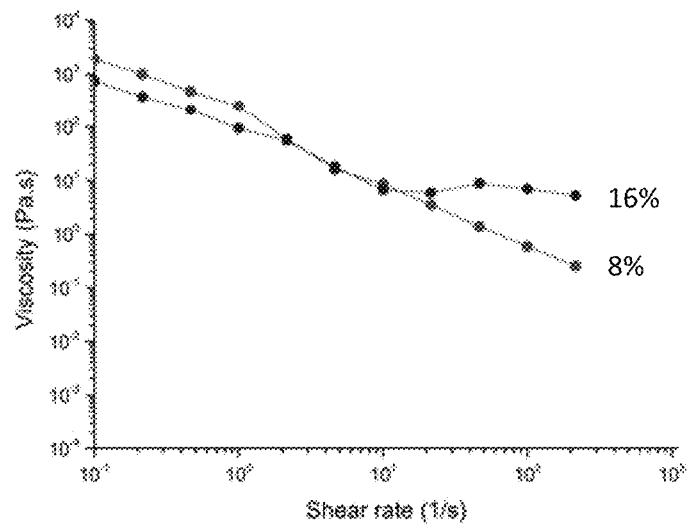
FIG. 3—Steady-Shear rheological measurements (frequency 1 Hz) for enzymatically cross-linked silk inks at different concentration (8% and 16% of silk solution).
Figure 4:
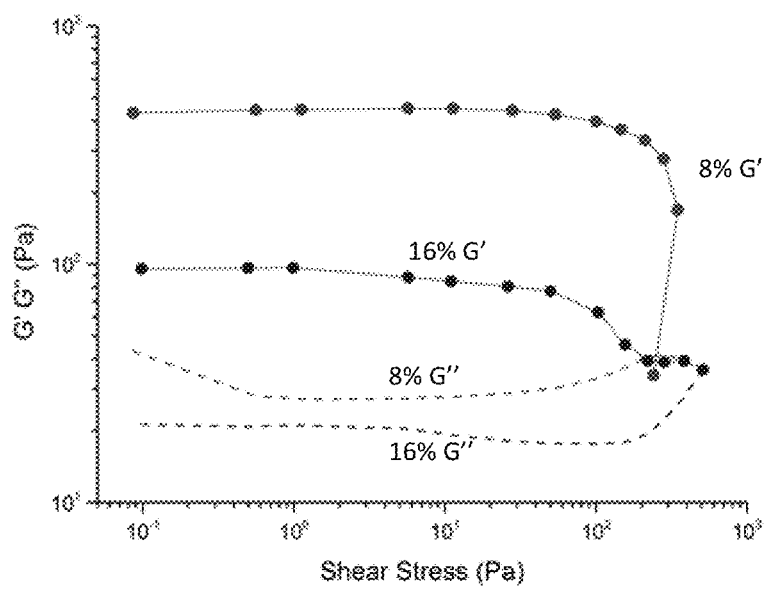
FIG. 4—Oscillatory rheological measurements (frequency 1 Hz) for enzymatically cross-linked silk inks at different concentration (8% and 16% of silk solution).
Figure 7:
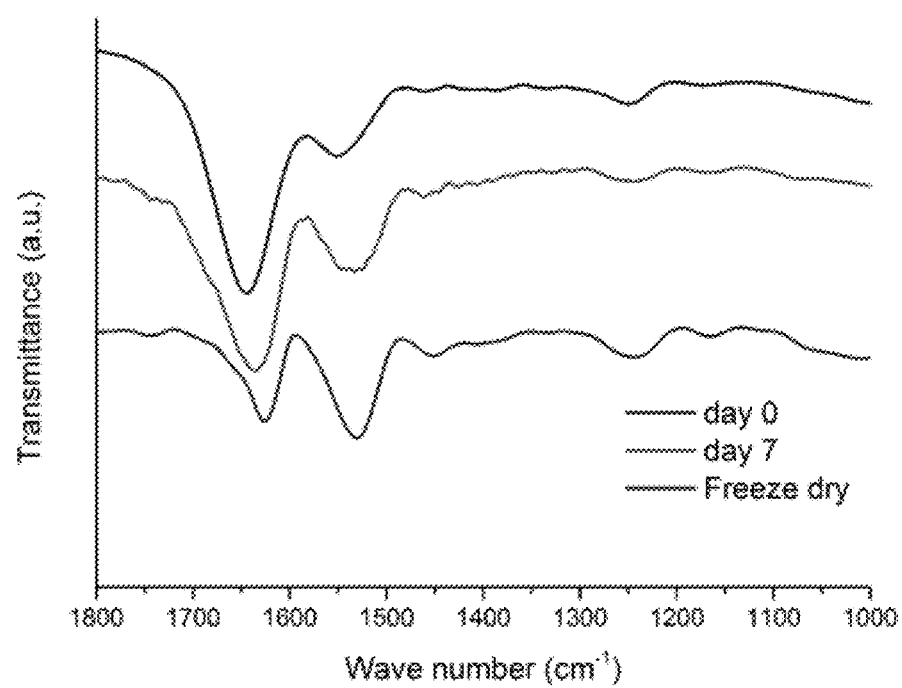
FIG. 7—ATR-FTIR spectra for the 3D structures after printing (day 0), after 7 days immersed in PBS (day 7), and after freeze drying (Freeze dry).

FIGS. 3 and 4 shows that bob silk inks present shear thinning properties. However, regarding FIG. 1, it is observed a high decrease of viscosity as the shear rate increases. The S18 ink presents higher viscosity at higher shear rates.

For both inks, the oscillatory measurements reveal an elastic behaviour at low shear rates (G'>G"). The dynamic yield stress can also be observed (G'=G").

Concerning the yield stress, the S16 ink presents a higher value, endorsing the previous results.

In an embodiment, the S16 ink was used in a 3D Bioplotter (Envisiotec) in order to print 3D Silk structures. The cartridge was previous prepared with S16 ink and further printed using a 22G nozzle. Square shape structures were printed (FIGS. 5A-5G). The structures have between 1 and 8 layers with a distance between strands of 1.5 mm.

In an embodiment, after printed, the structures were frozen at −80° C. and freeze-dried (FIGS. 6A-6D).

In an embodiment, the characterization of 3D structures was carried out as follows. Since, the silk ink can be used for many different applications, it was chosen to define two different strategies that will allow in the future to develop cellular and acellular 3D structures. As described above, one strategy consists in freeze dry the 3D structures (acellular strategy) and the other consists in the immersion directly in PBS (cellular strategy).

In an embodiment, ATR-FTIR analysis are presented to understand the conformation of the 3D structures, Dynamic mechanical analysis to access the mechanical properties, Scanning electronic microscopy and Micro-CT to understand the structures architecture after freeze-drying.

With these results, a new strategy to use silk as a bioink for 3D printing is disclosed.

Figure 11:
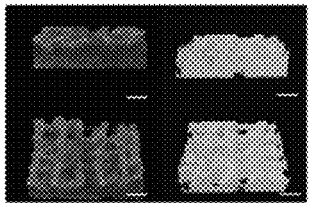
FIG. 11—Micro-CT results of 3D Structures after freeze dry. Scale bar: 500 μm.

In an embodiment, the mean porosity is defined as the percentage of pores of the structure. This was determined by micro-CT (see FIG. 11).

In an embodiment, the mean porosity of the microporosity is defined as 26.1±3.2%. This was determined by micro-CT.

In an embodiment, the mean porosity of the macroporosity is defined as 33.1±6.3%. This was determined by micro-CT.

In an embodiment, the mean porosity of the total porosity is defined as 59.1±3.4%. This was determined by micro-CT.

In an embodiment, the mean pore size is defined as 224.4±29. μm. This was determined by micro-CT.

In an embodiment, the mean trabecular thickness is defined as 47.8±2.8 μm. This was determined by micro-CT.

In an embodiment, dynamic mechanical analyses (DMA) were conducted as follows: the viscoelastic measurements were performed using a TRITEC8000B dynamic mechanical analyzer (Triton Technology, UK) in the compressive mode. The measurements were carried out at 37° C. The geometry of the samples was measured (measured each sample accurately with a micrometer) and the samples were clamped in the DMA apparatus and immersed in PBS solution. After equilibration at 37° C., the DMA spectra were obtained during a scan between 0.1 and 10 Hz.

Figure 8:
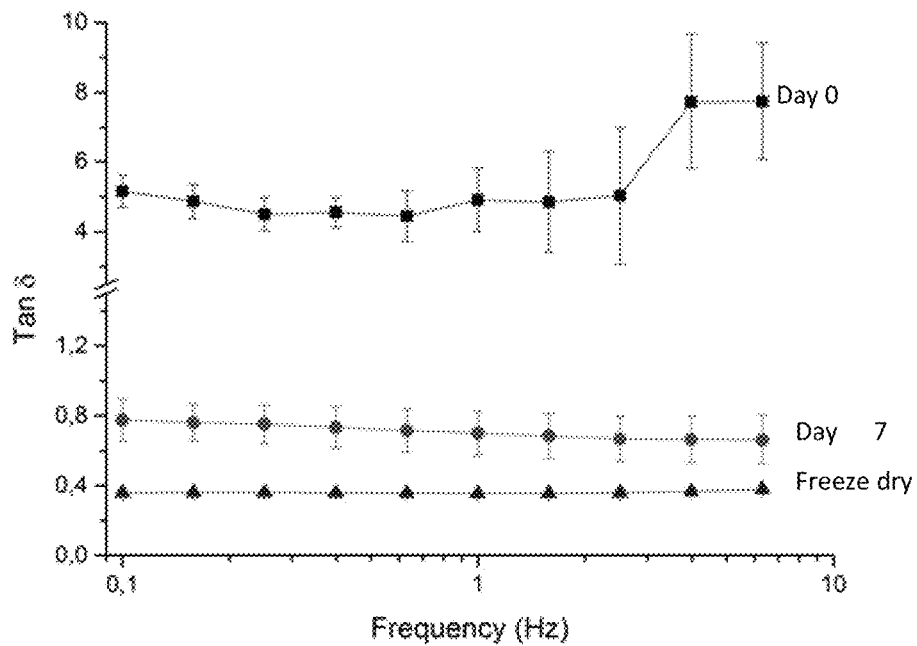
FIG. 8—Loss moduli (tan δ) of the 3D structures obtained by DMA, tested at 37° C. in PBS.

In an embodiment, FIG. 8, the damping properties (tan δ) are represented. The damping properties represents the ability to disperse energy, ie, softer structures have more damping properties than harder structures. That is what has been confirmed, as the material after printing (day 0) have higher values than after 7 days or after freeze drying.

Figure 9:
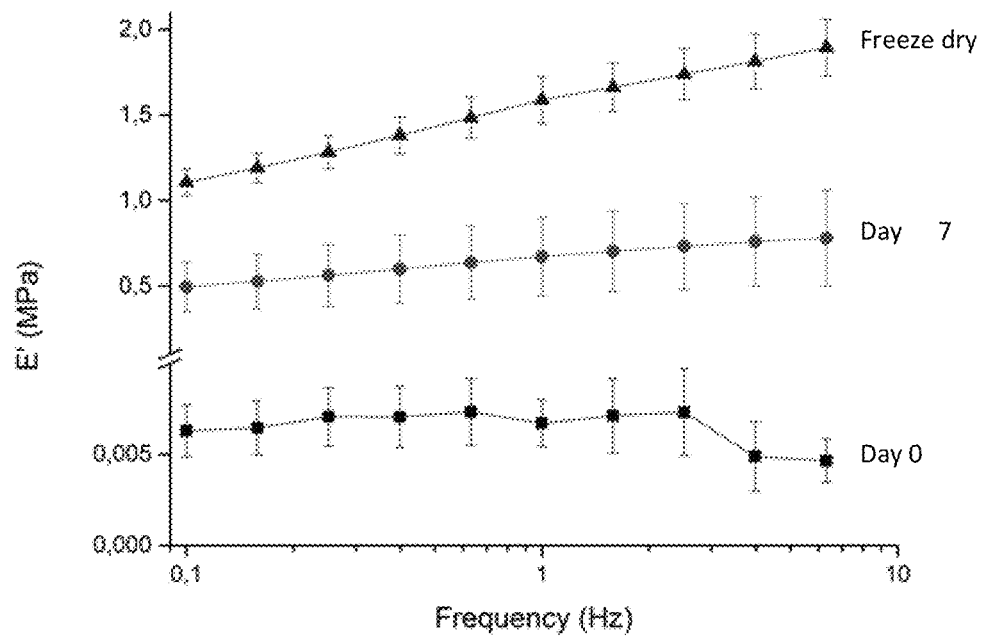
FIG. 9—Storage modulus (E') of the 3D structures obtained by DMA, tested at 37° C. in PBS.
Figure 10A:
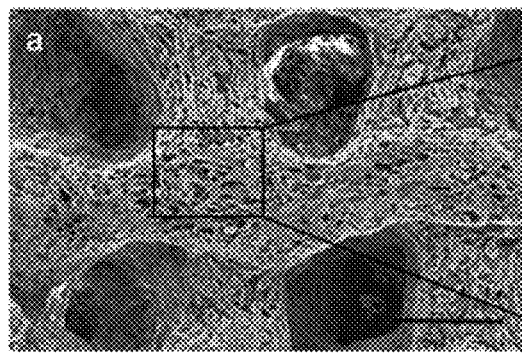
FIGS. 10A-10C—SEM images of the 3D structures after freeze-drying. Scale bars: 500 μm (FIGS. 10A and 10B), and 100 μm (FIG. 10C).
Figure 10C:
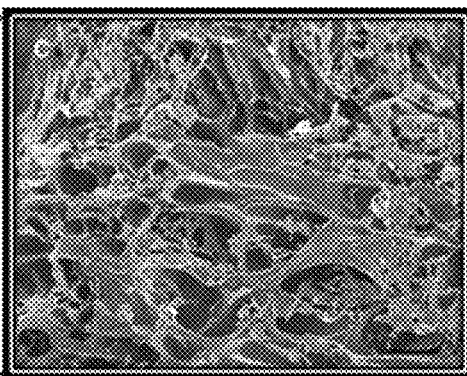
Figure 10B:
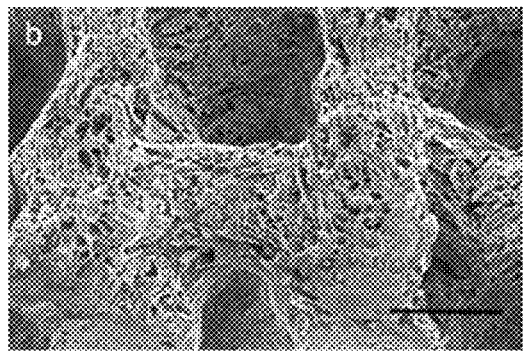

In an embodiment, FIG. 9, the storage modulus is represented. The storage modulus is related to the hardness of the material. Higher results of the hardness of the material may be obtained for freeze-drying material, in contrast with the material at day 0 or day 7.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

REFERENCES

1. Murphy S V, Atala A. 3D bioprinting of tissues and organs. Nat Biotech. 2014; 32(8):773-85.
2. Kang H-W, Lee S J, Ko I K, Kengla C, Yoo J J, Atala A. A 3D bioprinting system to produce human-scale tissue constructs with structural integrity. Nat Biotech. 2016; 34(3):312-9.
3. Moreira Teixeira L S, Feijen J, van Blitterswijk C A, Dijkstra P J, Karperien M. Enzyme-catalyzed crosslinkable hydrogels: Emerging strategies for tissue engineering. Biomaterials. 2012; 33(5):1281-90.

The invention claimed is:

1. A 3-D printing ink comprising a silk fibroin enzymatically cross-linked hydrogel comprising 11-20% (v/v) of an aqueous solution of silk fibroin, wherein the molecular weight of the silk fibroin is 300-350 kDa, and wherein the ink has a partial β-sheet conformation.

2. The ink of claim 1, wherein the ink comprises 11-15% (v/v) of the aqueous solution of silk fibroin.

3. The ink of claim 1, further comprising 0.1-10% (m/v) of keratin.

4. The ink of claim 1, further comprising 0.1-10% (m/v) of elastin.

5. The ink of claim 1, wherein the ink has a viscosity of 100 kilopascal-seconds (kPa·s$^{-1}$)-0.1 pascal-second (Pa·s$^{-1}$) as a function of shear rate at 25° C.

6. The ink of claim 1, wherein the ink has a loss modulus (G') of 50-1500 Pa at 25° C.

7. The ink of claim 1, wherein the ink has a storage modulus (G") of 10-100 Pa at 25° C.

8. The ink of claim 3, wherein the molecular weight of the keratin is 40-60 kDa.

9. The ink of claim 4, wherein the molecular weight of the elastin is 40-60 kDa.

10. The ink of claim 1, wherein the hydrogel is a capsule, fibre, coating, membrane, particle, scaffold, medical device, microfluidic device or patient-specific implant.

* * * * *